United States Patent [19]

Manis et al.

[11] Patent Number: 5,685,967

[45] Date of Patent: Nov. 11, 1997

[54] COATED PLASTIC MOLD FOR ELECTROPHORESIS GEL

[75] Inventors: David J. Manis, Del Mar; Sheldon Engelhorn, Encinitas, both of Calif.

[73] Assignee: Novel Experimental Technology, San Diego, Calif.

[21] Appl. No.: 573,620

[22] Filed: Dec. 18, 1995

Related U.S. Application Data

[63] Continuation of Ser. No. 242,615, May 13, 1994, abandoned.

[51] Int. Cl.$^6$ ............................................. B01D 61/42
[52] U.S. Cl. ............................................. 204/616; 204/606
[58] Field of Search ............................. 204/606, 615, 204/616

[56] References Cited

U.S. PATENT DOCUMENTS

| | | | |
|---|---|---|---|
| 3,442,686 | 5/1969 | Jones | 117/70 |
| 4,548,869 | 10/1985 | Ogawa et al. | 428/474.7 |
| 4,548,870 | 10/1985 | Ogawa et al. | 428/474.7 |
| 4,579,783 | 4/1986 | Ogawa et al. | 428/475.2 |
| 4,600,641 | 7/1986 | Ogawa et al. | 428/355 |
| 4,718,998 | 1/1988 | Ogawa et al. | 204/299 |
| 4,722,777 | 2/1988 | Ogawa et al. | 204/299 R |
| 4,737,258 | 4/1988 | Ogawa et al. | 204/299 |
| 4,737,259 | 4/1988 | Ogawa et al. | 204/299 |
| 4,897,306 | 1/1990 | Sugimoto et al. | 428/336 |
| 4,954,236 | 9/1990 | Kushner et al. | 204/299 R |
| 5,084,356 | 1/1992 | Deak et al. | 428/458 |
| 5,085,904 | 2/1992 | Deak et al. | 428/35.7 |
| 5,224,441 | 7/1993 | Felts et al. | 118/718 |

FOREIGN PATENT DOCUMENTS

| | | |
|---|---|---|
| 0 299 754 A2 | 1/1989 | European Pat. Off. . |
| 62-247244 | 10/1987 | Japan . |
| WO 90/13020 | 11/1990 | WIPO . |

OTHER PUBLICATIONS

A. Andrews, Electrophoresis, pp. 5–24 (2nd ed. Oxford University Press, 1986).

B. Hames and D. Rickwood, Gel Electrophoresis of Proteins, pp. 1–50 (2nd ed. Oxford University Press, 1990).

J. Felts, Transparent Gas Barrier Technologies (Airco Coating Technology), date not available.

A. Rizika, Vapor Coating with SiOx: The Flexible Glass Barrier (Presented at Pack Expo '92 Conference, Chicago, Nov. 8–11, 1992) (Airco Coating Technology).

*Primary Examiner*—John Niebling
*Assistant Examiner*—Brendan Mee
*Attorney, Agent, or Firm*—Fish & Neave

[57] ABSTRACT

An improved coated plastic mold for the polymerization of electrophoresis gels. The mold controls the effects of oxygen contamination upon gel polymerization resulting in a more uniform gel with improved properties.

17 Claims, 2 Drawing Sheets

COATED PLASTIC MOLD FOR ELECTROPHORESIS GEL

This is a continuation of application Ser. No. 08/242,615 filed on May 13, 1994 and titled Coated Plastic Mold For Electrophoresis Gel, now abandoned.

This invention relates to gel electrophoresis. More particularly, this invention relates to a novel coated plastic gel mold for casting electrophoresis gels.

BACKGROUND OF THE INVENTION

Gel electrophoresis is a common procedure for the separation of biological molecules, such as DNA, RNA, polypeptides and proteins. In gel electrophoresis, the molecules are separated into bands according to the rate at which an imposed electric field causes them to migrate through a filtering gel.

The basic apparatus used in this technique consists of a gel enclosed in a glass tube or sandwiched as a slab between glass or plastic plates. The gel has an open molecular network structure, defining pores which are saturated with an electrically conductive buffered solution of a salt. These pores are large enough to admit passage of the migrating macromolecules through the gel.

The gel is placed in a chamber in contact with buffer solutions which make electrical contact between the gel and the cathode or anode of an electrical power supply. A sample containing the macromolecules and a tracking dye is placed on top of the gel. An electric potential is applied to the gel causing the sample macromolecules and tracking dye to migrate toward the bottom of the gel. The electrophoresis is halted just before the tracking dye reaches the end of the gel. The locations of the bands of separated macromolecules are then determined. By comparing the distance moved by particular bands in comparison to the tracking dye and macromolecules of known mobility, the mobility of other macromolecules can be determined. The size of the macromolecule can then be calculated.

The rate of migration of macromolecules through the gel depends upon three principle factors: the porosity of the gel; the size and shape of the macromolecule; and the charge density of the macromolecule. It is critical to an effective electrophoresis system that these three factors be uniform within a particular gel and reproducible from gel to gel and from sample to sample. However, maintaining uniformity is difficult because each of these factors is sensitive to many variables in the chemistry of the gel system.

Polyacrylamide gels are commonly used for electrophoresis. Other gels suitable for electrophoresis include agarose gels and starch gels. Polyacrylamide gel electrophoresis or PAGE is popular because the gels are optically transparent, electrically neutral and can be made with a range of pore sizes.

The porosity of a polyacrylamide gel is in part defined by the total percentage of acrylamide monomer plus crosslinker monomer ("% T") it contains. The greater the concentration, the less space there is between strands of the polyacrylamide matrix and hence the smaller the pores through the gel. An 8% polyacrylamide gel has larger pores than a 12% polyacrylamide gel. An 8% polyacrylamide gel consequently permits faster migration of macromolecules with a given shape, size and charge density. When smaller macromolecules are to be separated, it is generally preferable to use a gel with a smaller pore size such as a 20% gel. Conversely, for separation of larger macromolecules, a gel with a larger pore size is often used, such as an 8% gel.

Pore size is also dependent upon the amount of crosslinker used to polymerize the gel. At any given total monomer concentration, the minimum pore size for a polyacrylamide gel is obtained when the ratio of total monomer to crosslinker is about 20:1, (the common expression for this ratio would be "5% C").

Methods of making PAGE gels are well known. See B. Hames and D. Rickwood, Gel Electrophoresis of Proteins (2d ed. Oxford University Press, 1990); A Andrews, Electrophoresis (2nd ed. Oxford University Press, 1986). In general, stock solutions containing acrylamide monomer, a crosslinker such as bisacrylamide, gel buffers and modifying agents such as sodium dodecyl sulphate ("SDS") are prepared. These stock solutions can be stored until a gel is needed. To manufacture a gel, the stock solutions are mixed with water in proportions according to the final desired concentrations of the various constituents.

The mixed stock solutions contain oxygen. Because oxygen inhibits polymerization, it is often desirable to reduce the amount of oxygen in the mixture. De-oxygenation permits a faster polymerization reaction. The mixture may be de-oxygenated by sparging the mixture with helium or nitrogen.

After the mixture has been de-oxygenated (if desired), the polymerization reaction is commenced. One way of inducing polymerization is by adding an agent to generate free radicals such as TEMED (N,N,N',N' tetramethylethylene diamine), APS (Ammonium Persulphate) or riboflavin. Addition of these reagents initiates a free radical-chain reaction in the solution causing the polymerization of acrylamide monomers and the crosslinking of the acrylamide chains with the bifunctional group such as bisacrylamide.

After addition of the polymerization initiator, the mixture is introduced into a gel mold to solidify. There are two basic configurations for gel electrophoresis, slab gel electrophoresis and rod gel electrophoresis. In slab gel electrophoresis, the gel mold typically consists of two plates clipped together over two spacers. In rod gel electrophoresis, the mold typically consists of a tube. To cast the gel, the mold is filled with a gel mixture while care is taken to avoid introduction of air bubbles. Often a layer of water is poured on top of the mixture to prevent entry of oxygen during polymerization.

Alternative methods of inducing polymerization and crosslinking of gels have been developed. These include processes such as photo-initiated polymerization and the like. In photo-initiated polymerization, a light-activated free-radical forming agent is used. The gel-forming mixture is introduced into the gel mold and then irradiated with light. The light induces free radical formation and causes polymerization and crosslinking of the monomers in the mixture.

Control of the polymerization reaction is critical to obtaining a reproducible gel of uniform pore size. One important factor affecting the polymerization reaction is the presence of oxygen. In free-radical induction of polymerization, polymerization does not commence until free oxygen has been removed from the mixture. For this reason, polymerization mixtures are often degassed to remove most of the oxygen prior to adding the polymerization initiators. Free oxygen not only inhibits the formation of free radicals; it also terminates growing acrylamide chains. Thus the presence of oxygen can affect polymerization in many gel systems including both chemical and photo-initiated polymerization systems.

Glass has typically been used to make molds for electrophoresis gels. However, glass suffers from the disadvantage that it is fragile, difficult to form into particular shapes, expensive and non-disposable. It is easier and more economical to form gel molds from plastic materials by processes such as injection molding. However, in attempting to use plastic molds for casting electrophoresis gels, applicants discovered the problem of decreased resolution of the separated macromolecule bands. This decreased resolution was caused by macromolecules moving faster on the surface of the gel in contact with the mold than in the interior of the gel. This variation in migration rates between the surface of the gel and the interior lead to smearing of the macromolecule bands. Initially this problem was thought to be caused by lack of adhesion between the gel and the mold. However, use of a hydrophilic mold with improved adhesion to the gel did not remedy the resolution problem.

On further investigation, applicants discovered that the resolution problem was caused by a local increase in the gel pore size near the mold surface as compared to the interior of the gel. This pore size variation was found to be the result of diffusion of oxygen from the surface of the plastic mold into the gel during the polymerization reaction. This diffusion caused a local increase in oxygen concentration in the gel mixture adjacent the mold surface and thus a local inhibition of polymerization resulting in the increased pore size observed at the gel surface.

SUMMARY OF THE INVENTION

It is an object of this invention to produce a plastic gel electrophoresis mold that facilitates uniform polymerization of an electrophoresis gel.

It is also an object of this invention to produce a plastic gel electrophoresis mold that inhibits diffusion of oxygen from the mold material into the gel during gel polymerization.

It is a further object of this invention to provide a relatively oxygen impermeable barrier between a plastic gel electrophoresis mold and an electrophoresis gel.

It is a further object of this invention to provide an oxygen barrier which is inert, stable, transparent and colorless.

In accordance with this invention, applicants describe an improved plastic electrophoresis gel mold which reduces local inhibition of gel polymerization by oxygen diffusion from the mold by providing an SiOx oxygen barrier between the plastic mold and the gel mixture. (SiOx refers to "SiO", "SiO$_2$" or mixtures of silicon oxides). The above and other objects and advantages of the present invention will be apparent upon consideration of the drawing and the following detailed description.

DETAILED DESCRIPTION OF THE INVENTION

Applicants describe an improved plastic electrophoresis gel mold which reduces local inhibition of gel polymerization by oxygen diffusion from the mold by providing an SiOx oxygen barrier between the plastic and the gel. In one embodiment of the invention, the mold is formed from two injection molded elements coated with a layer of SiOx upon their interior surfaces and then joined together. The SiOx layer preferably has an oxygen transmission rate of less than 2 cc/m$^2$-atm-day and the SiOx layer preferably has an oxygen permeability of not more than 1 cc-mil/m$^2$-atm-day.

Figure 1:
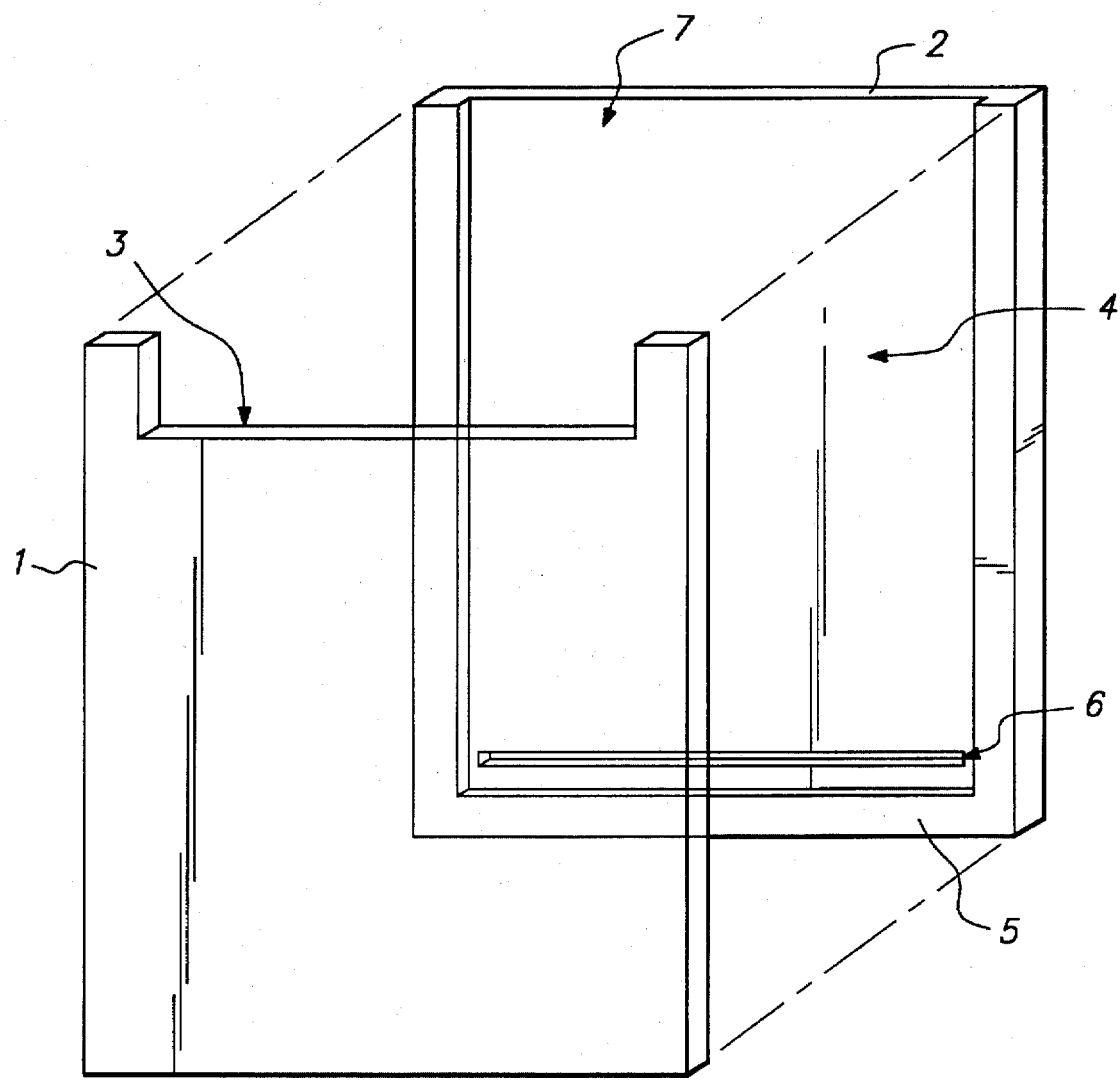
FIG. 1 is a perspective view of an embodiment of a gel mold of the present invention indicating the surfaces to be coated.

Referring to FIG. 1 the gel mold comprises two plastic plates 1 and 2. The plates can be formed by a process such as injection molding. Many different plastics are suitable for forming these plates. Suitable plastics for forming electrophoresis gel molds include polymers such as polyethylene terephthalate, polyvinyl chloride, polymethyl methacrylate, polystyrene, polyethylene, polymethyl polypropylene and cellulose acetates or any of their various co-polymers. The provision of the SiOx layer allows great flexibility in the choice of material for forming the support because it acts as a barrier between the material and the electrophoresis gel. It is desirable that the plastic be transparent so that the progress of the tracking dye through the gel can be easily monitored. If the gel mold is to be self-supporting it is also desirable that the plastic in at least portions of the mold be sufficiently rigid to support the gel.

Referring to FIG. 1, plastic plates 1 and 2 are shown having interior surfaces 3 and 4 respectively. Plate 2 is also shown to have a U-shaped raised spacer 5 which provides the contact with plate 1 and spaces the interior surface of plate 1 from the interior surface of plate 2. When the two plates are joined, the interior surfaces form a slab shaped cavity which is sealed by the raised spacer 5 except for the slot 6 at the lower end of plate 2 and the top opening 7 between plates 1 and 2. The thickness of the cavity is determined by the height of the raised spacer 5.

During preparation of a gel, the slot 6 in plate 2 is sealed. The gel mold is held vertically and gel-forming mixture is poured through the top opening 7 into the cavity between plates 1 and 2. Thus, during polymerization, the gel mixture is in contact with the interior surfaces 3 and 4 of plates 1 and 2.

The interior surfaces 3 and 4 of plates 1 and 2 are provided with a layer of SiOx which forms an oxygen barrier that reduces diffusion of oxygen from the surface of the plastic plates into the gel during polymerization. This SiOx coating is preferably uniform to prevent significant local variations in the rate of oxygen diffusion. The SiOx coating is also preferably transparent and colorless to allow observation of the gel during electrophoresis.

Figure 2:
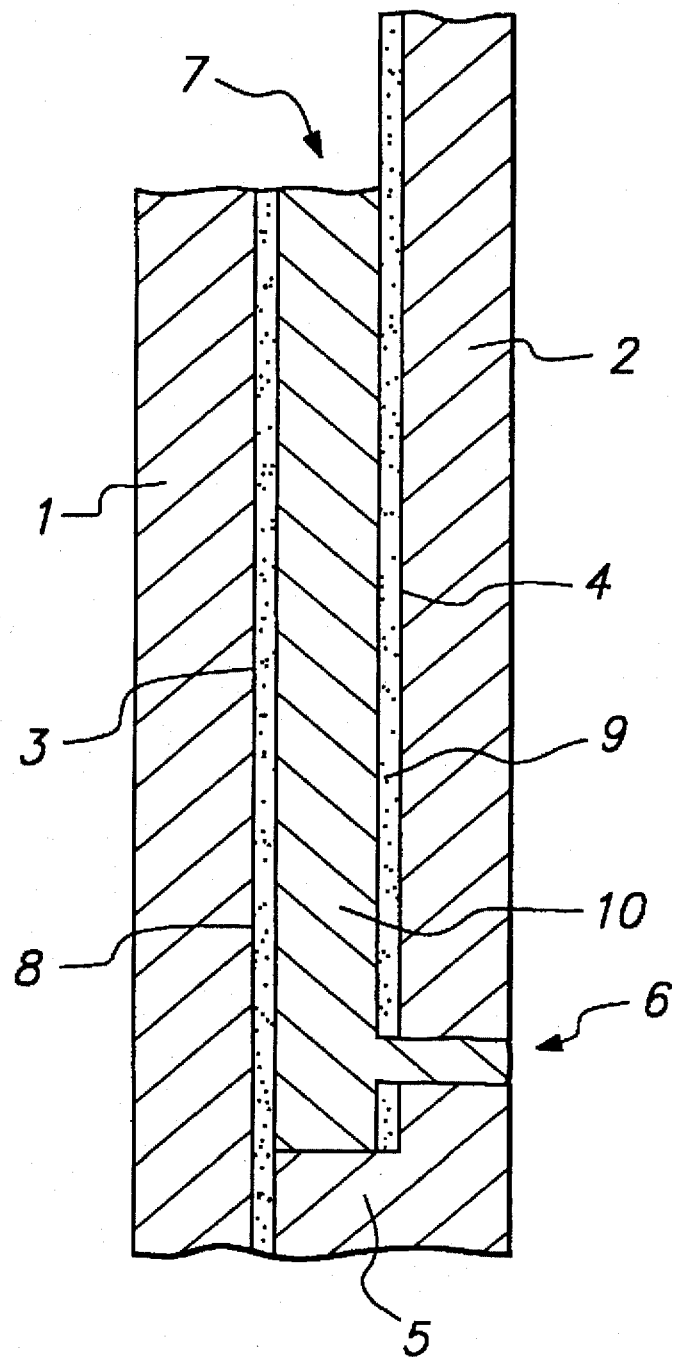
FIG. 2 is a cross-sectional view of the gel mold of FIG. 1 containing an electrophoresis gel.

Referring to FIG. 2, a cross section of the coated mold of FIG. 1 is shown containing an electrophoresis gel 10. The SiOx layers 9 and 10 on interior surfaces 3 and 4 of plates 1 and 2 are disposed between the plastic plates and the electrophoresis gel forming an oxygen barrier. The cross section is not drawn to scale as a range of thicknesses are possible for the SiOx layer and plates 1 and 2.

An alternative embodiment of a plastic gel mold within the scope of this invention could comprise one plastic plate and one glass plate. The plastic plate would be provided with a layer of SiOx on its interior surface as described. The plastic plate would be fixed to the glass plate to form the mold and allow for gel polymerization. A second alternative embodiment of a plastic gel mold could comprise a single plastic element, such as a tube, defining a cavity. The interior surface defining the cavity would be provided with a layer of SiOx. Many other configurations of gel molds are possible; each has in common a means for supporting and containing the gel mixture during polymerization. If the support structure is plastic, an advantage will be gained by providing a layer of SiOx between the plastic support structure and the gel to provide a oxygen barrier during polymerization.

An SiOx layer can be deposited onto plastic under vacuum by several processes including evaporative deposition, sputter deposition, chemical vapor deposition and plasma-enhanced chemical vapor deposition. In evaporative deposition, SiO or $SiO_2$ is heated in a vacuum chamber using a conventional heater or an electron beam. The SiOx material vaporizes and condenses on the plastic surface. The plastic is cooled to prevent degradation during this process. This method of coating is disclosed for example in U.S. Pat. No. 3,442,686.

In sputter deposition, an ionized plasma containing argon is used to bombard a cathode made of SiO or $SiO_2$. The plasma argon atoms knock atoms from the SiOx target which are then deposited onto the cooled surface of a plastic material facing the target.

In plasma-enhanced chemical vapor deposition, an SiOx coating is formed on a plastic surface by a chemical reaction in the evacuated coating chamber. A silicon containing gas (such as tetramethyldisiloxane or hexamethyldisiloxane) is flowed into the vacuum chamber along with oxygen and inert ballast gas such as helium. Power is applied to the system creating a plasma in which the silicon containing gas is oxidized and SiOx is deposited on the plastic surface within the chamber. This method of coating is disclosed for example in EPO publication 0299754 A2.

Each of these coating methods results in the deposition of an SiOx layer upon a plastic surface. Typically these SiOx layers will be less than about 5000 $A^o$ in thickness. The composition of the coating can be varied by controlling oxygen flowing into the vacuum deposition chamber. The deposition must be regulated to provide a uniform SiOx layer across the plastic surface. The thickness of the film required to achieve the desired oxygen barrier properties will depend upon the particular deposition process and deposition parameters used.

An SiOx layer deposited as described above can be applied to a gel mold in several different ways. In one method, the SiOx layer is deposited directly onto the interior surfaces of plastic plates such as 1 and 2. The plastic plates are introduced to the vacuum chamber where the SiOx coating is deposited directly onto their surface. Alternatively, the SiOx layer can be deposited onto a thin plastic film which is applied to the interior surface of the gel mold by bonding or laminating.

EXAMPLES

Tris (tris-hydroxy-amino-methane) and glycine were purchased from Research Organics (Cleveland OH). All other chemicals were reagent, "ultra pure" or "electrophoresis grade" from standard sources. To prepare the separating gel, the stock solutions were blended with ultra pure water to a final concentration 18% T, 2.5% C, 0.375M Tris-Cl pH 8.6, 3% (w/w) glycerol and 0.2 ul/ml TEMED. After degassing, 2.1 ul/ml of a 10% solution of APS was added, the solution was immediately poured into the cassette. The stacking gel was prepared in the same fashion as the separating gel, except that the final concentration obtained was 4% T, glycerol was omitted, the TEMED concentration was increased to 1.08 ul/ml and the APS increased to 10.35 ul/ml. The separating gel solution was poured into the gel mold then the stacking solution was immediately and carefully poured on top. A ten-well plastic comb, molded from polycarbonate (NOVEX, San Diego, Calif.), was then inserted into the opening 7, to form the wells and protect the top surface of the gel from contact with air. Polymerization was allowed to proceed for at least 60 minutes at room temperature.

Running buffer consisted of 25 mM Tris, 192 mM glycine and 0.1% SDS. Samples containing a set of protein standards and various concentrations of Tris HCl, glycerol and tracking dyes were heated for 15 min @ 70° C. before application. Bovine serum albumin (BSA), chicken ovalbumin, alkylated porcine insulin A and B chain, soybean trypsin inhibitor, and bovine erythrocyte carbonic anhydrase were included in the standard. Sample volume was 5 ul in all cases.

Gels were cast in 1 mm thickness mini-gel cassettes (Novex, San Diego, Calif.) either uncoated, or provided with an SiOx barrier deposited by plasma-enhanced chemical vapor deposition. Samples of the protein standards were then applied to the gels. The gels were run in a minicell (Novex, San Diego Calif.) to examine the quality of the electrophoresis gel.

Example 1

A gel was poured in an uncoated mini-gel cassette injection molded out of SAN (styrene acrylonitrile). Polymerization of the gel was very poor with some portions remaining unpolymerized. Attempts to use the gel for electrophoresis yielded very poor results with little or no protein band resolution possible. The oxygen transmission rate of the uncoated cassette was found to be approximately 60 $cc/m^2$-atm-day. The oxygen permeability of SAN is approximately 4000 $cc$-$mil/m^2$-atm-day.

Example 2

A gel was poured in an uncoated mini-gel cassette injection molded out of Barex 210 (BP Chemicals International, Cleveland Ohio). Polymerization of the gel was good. Attempts to use the gel for electrophoresis yielded good results but with protein bands exhibiting moderate resolution because of band smearing. The oxygen transmission rate of the uncoated cassette was found to be approximately 0.2 $cc/m^2$-atm-day. The oxygen permeability of hydrated Barex is approximately 14 $cc$-$mil/m^2$-atm-day.

Example 3

A gel was poured in an uncoated mini-gel cassette similar to the type in Example 1 except that it was injection molded from methacrylate. Slightly higher APS and TEMED concentrations were employed. Attempts to use the gel for electrophoresis yielded mediocre results with protein bands exhibiting obvious smearing. A cross section of the gel revealed larger pores on the surface of the gel as compared to the interior. The oxygen transmission rate of the uncoated acrylic cassette was found to be approximately 6 $cc/m^2$-atm-day. The oxygen permeability of acrylic is approximately 400 $cc$-$mil/m^2$-atm-day.

Example 4

A gel was poured in a mini-gel cassette of the same type as in Example 1 molded from SAN except that the interior surfaces of the cassette had been directly coated with a layer of SiOx by plasma-enhanced chemical vapor deposition. Unlike in Example 1, the gel polymerized. However, attempts to use the gel for electrophoresis yielded poor results with protein bands exhibiting pronounced smearing. The gel also showed smudging indicative of incomplete polymerization. The oxygen transmission rate of the coated cassette was found to be approximately 30 $cc/m^2$-atm-day. The oxygen transmission rate of the SiOx layer was thus estimated to be about 60 $cc/m^2$-atm-day.

Example 5

A gel was poured in a mini-gel cassette of the same type as in Example 4 except that a denser layer of SiOx had been applied. Polymerization of the gel was again much improved over the uncoated cassette of Example 1. Attempts to use the gel for electrophoresis yielded excellent results with protein bands exhibiting no visible smearing. The results indicate uniform pore size due to an effective oxygen barrier. The oxygen transmission rate of the coated cassette was found to be 1 cc/m$^2$-atm-day. The oxygen transmission rate of the SiOx layer was thus calculated to be approximately 1 cc/m$^2$-atm-day. The oxygen permeability of the SiOx layer was about 0.005 cc-mil/m$^2$-atm-day.

Example 6

A gel was poured in a mini-gel cassette of the same type as in Example 1 except that an SiOx coated polyethylene terephthalate (PET) film was bonded to the interior surfaces of the cassette with the SiOx layer facing away from the plastic plates. The results were similar to Example 5, with good resolution indicating uniform pore size due to an effective oxygen barrier. The coated PET film had an oxygen transmission rate of 1 cc/m$^2$-atm-day. The oxygen transmission rate of the SiOx layer was approximately 1 cc/m$^2$-atm-day. The oxygen permeability of the SiOx layer was about 0.002 cc-mil/m$^2$-atm-day.

Example 7

A gel was poured in a mini-gel cassette of the same type constructed as in Example 6 except that the SiOx coated PET film was bonded to the plates with the SiOx layer adjacent the plastic plate. The results were similar to Example 3; the gel polymerized completely but resolution was only fair. The coated film was identical to that used in Example 6 and thus the oxygen transmission rate of the film was also 1 cc/m$^2$-atm-day and the oxygen transmission rate of the SiOx layer was also approximately 1 cc/m$^2$-atm-day. However, the oxygen permeability the layer adjacent the gel, in this case PET, was about 100 cc-mil/m$^2$-atm-day.

These examples demonstrate the efficacy of using a SiOx oxygen barrier to improve polymerization of electrophoresis gels in a plastic gel mold. The amount of SiOx that needs to be applied in a particular situation is determined by the amount of oxygen that will diffuse from a particular plastic gel mold material during polymerization and also by the sensitivity of the particular gel process to the presence of oxygen.

These examples also indicate that the permeability of the surface in contact with the gel is more important than the total oxygen transmission rate of the mold. Notably, the Barex cassette of Example 2, which had the lowest oxygen transmission rate, failed to provide an effective oxygen barrier. Applicants concluded that, due to the higher permeability of Barex, oxygen saturating the Barex mold was able to diffuse from the surface of the mold adjacent the gel into the gel during polymerization.

Furthermore, the oxygen transmission rates of the cassettes in Examples 6 and 7 were identical but much better resolution was obtained in Example 6. Applicants concluded that in Example 7 oxygen saturating the PET layer was able to diffuse into the gel during polymerization. The better results of example 6 were obtained because of the low permeability of the material adjacent the gel.

For applications such as food packaging, a material's inhibition of oxygen transmission over a period of weeks is important and thus the oxygen transmission rate provides a true measure of efficacy. However, for the purpose of coating an electrophoresis mold, applicants concluded that the important factor is the amount of oxygen the gel can absorb from the mold during the critical minutes of polymerization. In an electrophoresis mold, the permeability of the layer adjacent the gel is the most important factor.

As seen in Examples 5 and 6, the provision of an SiOx layer provides an effective oxygen barrier despite the fact that the oxygen transmission rates of the SiOx coated cassettes were higher than the Barex cassette of Example 2. This efficacy stems from the very low permeability of the layer contacting the gel (approximately 0.002 cc-mil/m$^2$-atm-day). Applicants conclude that for oxygen barrier properties effective to prevent variations in gel polymerization, the oxygen barrier layer should have an oxygen permeability of no more than about 1 cc-mil/m$^2$-atm-day and should have an oxygen transmission rate of no more than 2 cc/m$^2$-atm-day.

While the invention has been explained in relation to its preferred embodiments, it is to be understood that various modifications thereof will become apparent to those skilled in the art. The foregoing disclosure is not intended or to be construed to limit the present invention, or to otherwise exclude any such other embodiments, adaptions, variations and equivalent arrangements, the present invention being limited only by the claims appended hereto and the equivalents thereof.

We claim:

1. A mold for an electrophoresis gel comprising:
   a plastic support structure having at least one interior surface defining a cavity; and
   an SiOx layer consisting essentially of SiOx disposed between at least a portion of said interior surface and said cavity;
   wherein the SiOx layer forms an oxygen barrier having an oxygen permeability of no more than 1 cc-mil/m$^2$-atm-day, and the SiOx layer has an oxygen transmission rate of no more than 2 cc/m$^2$-atm-day.

2. A mold as in claim 1 wherein the SiOx layer is deposited directly onto the interior surface of said plastic support structure.

3. A mold as in claim 1 wherein the SiOx layer is deposited onto a plastic film bonded to the interior surface of said plastic support structure.

4. A medium for electrophoresis as in claim 1 wherein said SiOx layer was deposited onto said plastic support by a vacuum deposition process.

5. A mold for an electrophoresis gel as in claim 1 wherein said plastic support structure has at least one interior surface defining a slab shaped cavity; and said SiOx layer is disposed between at least a portion of said interior surface defining one surface of a slab and said cavity and between at least another portion of said interior surface defining the opposite surface of a slab and said cavity.

6. A mold for an electrophoresis gel as in claim 1 wherein said plastic support structure has at least one interior surface defining a rod shaped cavity; and said SiOx layer is disposed between substantially all of said interior surface and said cavity.

7. A mold for an electrophoresis gel as in claim 1 wherein said plastic support structure has at least one interior surface defining a cavity; and said SiOx layer is disposed between substantially all of the portion of said interior surface corresponding to those parts of a gel that may substantially contact molecules to be separated during electrophoresis, and said cavity.

8. A medium for electrophoresis comprising:
   a plastic support structure defining a cavity;
   an aqueous electrophoresis gel within said cavity; and an oxygen barrier disposed between said plastic support structure and said aqueous electrophoresis gel;

wherein said oxygen barrier comprises a layer including an SiOx layer consisting essentially of SiOx; and wherein said SiOx layer has an oxygen permeability no more than 0.01 cc-mil/m$^2$-atm-day, and said SiOx layer has an oxygen transmission rate of no more than 2 cc/m$^2$-atm-day.

9. A medium for electrophoresis as in claim 8 wherein said SiOx layer was deposited directly onto the interior surface of said plastic support structure.

10. A medium for electrophoresis as in claim 8 wherein said SiOx layer was deposited onto a plastic film bonded to the interior surface of said plastic support structure.

11. A medium for electrophoresis as in claim 8 wherein said oxygen barrier comprises a layer of inorganic oxide deposited onto said plastic support by a vacuum deposition process.

12. A medium for electrophoresis comprising:

a plastic support;

an aqueous electrophoresis gel;

an oxygen barrier disposed between said plastic support and said aqueous electrophoresis gel;

wherein the permeability of said oxygen barrier is less than 1 cc-mil/m$^2$-atm-day, and wherein said oxygen barrier has an oxygen transmission rate of no more than 2 cc/m$^2$-atm-day; and wherein said oxygen barrier comprises an inorganic oxide selected from the group consisting of SiO and SiO$_2$.

13. A medium for electrophoresis as in claim 12 wherein said oxygen barrier comprises a layer consisting essentially of one or more inorganic oxides selected from the group consisting of SiO and SiO$_2$.

14. A medium for electrophoresis as in claim 12 wherein said oxygen barrier comprises a layer of inorganic oxide deposited onto said plastic support by a vacuum deposition process.

15. A medium for electrophoresis as in claim as in claim 12 wherein said plastic support has at least one interior surface defining a slab shaped cavity; said aqueous electrophoresis gel is a slab gel; and said oxygen barrier is disposed between at least a portion of said interior surface and a portion of one side of said gel and between at least another portion of said interior surface and a portion of the opposite side of said gel.

16. A medium for electrophoresis as in claim as in claim 12 wherein said plastic support structure has at least one interior surface defining a rod shaped cavity; said aqueous electrophoresis gel is a rod gel; and said oxygen barrier is disposed between substantially all of said interior surface and said gel.

17. A medium for electrophoresis as in claim as in claim 12 wherein said plastic support structure has at least one interior surface defining a cavity; and said oxygen barrier is disposed between substantially all of the portion of said interior surface corresponding to those parts of a gel that may substantially contact molecules to be separated during electrophoresis, and said gel.

* * * * *